United States Patent [19]

Nelson et al.

[11] 3,941,784

[45] Mar. 2, 1976

[54] PRODUCTION OF CHLOROCYANURIC ACID

[75] Inventors: George D. Nelson, Creve Coeur; Kenneth J. Nissing, St. Charles; William F. Symes, Webster Groves, all of Mo.

[73] Assignee: Monsanto Company, St. Louis, Mo.

[22] Filed: Dec. 26, 1974

[21] Appl. No.: 536,499

[52] U.S. Cl. ............................................. 260/248 C
[51] Int. Cl.² ..................................... C07D 251/28
[58] Field of Search ............................... 260/248 C

[56] References Cited
UNITED STATES PATENTS 3,806,507  4/1974  Sawhill ............................. 260/248

*Primary Examiner*—John M. Ford
*Attorney, Agent, or Firm*—William H. Duffey

[57] ABSTRACT

Chlorocyanuric acid of increased particle size is obtained by reacting cyanuric acid, alkali metal hydroxide and chlorine in an aqueous reaction mixture in the presence of a promoter selected from the group consisting of polyoxyethylene, polyoxypropylene and polyoxyethylene-polyoxypropylene copolymers.

8 Claims, No Drawings

PRODUCTION OF CHLOROCYANURIC ACID

BACKGROUND OF THE INVENTION

1. Field of the Invention

The present invention relates to an improved process for manufacturing chlorocyanuric acids (including chloroisocyanuric acids), particularly trichloroisocyanuric acid and dichloroisocyanuric acid. More specifically, this invention pertains to a method for preparing chlorocyanuric acids having increased particle size.

2. Description of the Prior Art

The preparation of chlorocyanuric acids such as trichlorocyanuric acid or dichlorocyanuric acid is well known in the prior art.

One method for producing chlorocyanuric acid is described in U.S. Pat. No. 2,969,360 issued Jan. 24, 1961. In this process, cyanuric acid is fed along with aqueous alkali (in molar ratio corresponding to the number of chlorine atoms to be attached) and chlorine to an aqueous reaction zone which is maintained at a pH no higher than 9. The feed ingredients are added in essentially stoichiometric proportions. The crude chlorocyanuric acid precipitates from the solution as a solid slurry. The slurry product is periodically filtered to separate the crystalline products from the mother liquor whereupon the crystalline product is dried.

Prior art processes for producing chlorocyanuric acid have been beset with numerous difficulties most of which are attributable to deficient particle size. For example, considerable manufacturing downtime and rate variances have been experienced in the manufacture of trichlorocyanuric acid due to difficulties in dewatering which result in a slushy feed to the dryer. When very wet or slushy product material reaches the dryer it becomes necessary to reduce the production rate or shut down the unit in order to avoid packaging wet trichlorocyanuric acid. The primary cause for this problem is believed to be the very fine particle size produced in the process.

The patent literature reports other problems attributable to small particle size such as those relating to product separation (filtration), washing and drying as well as those relating to handling of the final dusty product. Small particle size is also said to decrease product stability.

It has been proposed heretofore in U.S. Pat. No. 3,120,522 issued Feb. 4, 1964, that chlorocyanuric acid crystals having increased size can be produced by adding to the reaction mixture from which these crystals are formed, from 50 to 1,000 ppm of a chlorinated hydrocarbon containing 1 to 6 carbon atoms and having not more than one hydrogen atom in its molecule.

It has further been proposed heretofore in U.S. Pat. No. 3,427,314 issued Feb. 11, 1969, that increased particle size can be achieved by heating trichlorocyanuric acid to from 130° to 225°C. with agitation and thereby causing the particles to agglomerate.

In addition, it has been proposed heretofore in U.S. Pat. No. 3,453,274 issued July 1, 1969, that crystal size of chlorocyanuric acids may be increased by adding from 50 ppm to 150 ppm of an alkali metal hydrocarbon sulfonate to the reaction mixture while maintaining the reaction mixture at a pH between 1.0 and 4.5.

The principal object of the present invention is to provide a superior chlorocyanuric acid product of increased particle size which overcomes many of the deficiencies experienced in the prior art, particularly the dewatering and drying problems. This object has been accomplished through use of certain promoters during the manufacturing process.

DESCRIPTION OF THE INVENTION AND PREFERRED EMBODIMENTS

The promoters, the novel application of which are the subject of this invention, are polymers and copolymers of ethylene oxide and/or propylene oxide. More specifically, the promoters are selected from the group consisting of polyoxyethylene, polyoxypropylene, and polyoxyethylene-polyoxypropylene copolymers. The terms "polyoxyethylene" and "polyoxypropylene", as employed herein, denote homopolymers of ethylene oxide and propylene oxide, respectively.

While the promoters of the present invention will be mainly described in connection with particle size promotion of trichlorocyanuric acid (or trichloroisocyanuric acid), their utility is not limited thereto. Superior results will likewise be illustrated hereafter in particle size promotion of dichlorocyanuric acid.

A preferred method of manufacturing trichlorocyanuric acid to which this invention is applicable is to mix a slurry of substantially pure cyanuric acid with alkali metal hydroxide (e.g., sodium or potassium hydroxide, preferably the former), to prepare an aqueous solution in which the sodium hydroxide to cyanuric acid ratio is about 3:1. The solution is then fed continuously to a reactor to which chlorine and the promoter are also fed continuously, while maintaining a temperature of the reactor contents at about 25°C. The promoter feed rate is adjusted to maintain a concentration of the promoter in the reactor at from about 20 to 500 ppm by weight and preferably about 100 to 300 ppm by weight, based upon the reactor contents.

The preferred promoters for use herein are polyoxyethylene-polyoxypropylene copolymers such as those marketed by BASF-Wyandotte Corporation under the trade name "Pluronic Polyols". Superior results have been achieved in the present process wherein the promoter is "Pluronic L-62" which is said by the manufacturer to have an average molecular weight of about 2,500 while being about 20% by weight ethoxylated (polyoxyethylene), the balance being essentially polyoxypropylene.

When using Pluronic L-62 promoter in the preferred process described above, the product of the process is withdrawn from the reaction as a slurry, then filtered, dried and packaged. When produced in this manner the particle size of the final product was such that 96% by weight was retained on a 79 mesh per centimeter screen as compared to only 65% by weight retention for product manufactured by the same method, but without employing the promoter.

The exact mechanism by which applicants' promoters achieve the superior results is not fully understood. It is unclear whether the promoter causes agglomeration of a plurality of discrete crystals or whether the crystals themselves are caused to enlarge in comparison to non-promoted crystals. Thus, since applicants do not wish to be bound by a single theory in explaining their unexpected results, the mechanism is merely described as one of "promotion" and the additive is simply called a "promoter". Even though applicants refer to "particle size", "particle size distribution" and "crystalline product" in their illustrative examples herein, these phrases are employed for convenience of description and should not be construed as restricting applicants' promotion mechanism to any single theory.

A further understanding of the advantages and processes of the present invention will be derived from the following examples which are intended to illustrate the invention but not to limit the scope thereof, parts and percentages being by weight unless otherwise specified.

EXAMPLE 1

This example illustrates a conventional preparation of trichlorocyanuric acid wherein the promoter of the present invention was not employed. A feed solution was prepared by mixing a cyanuric acid slurry with sodium hydroxide to produce a solution containing 7.6 percent cyanuric acid with a mole ratio of sodium hydroxide to cyanuric acid of 3.2:1. The chlorination reaction was provided for by a jacketed 1.4 liter glass reactor equipped with a stirrer, side arm for product overflow, subsurface feed tube and a fritted glass sparger. Starting with water in the reactor, feed solution is introduced through the feed tube at about 40 ml./min. and chlorine is introduced through the sparger at about 5.5 grams per minute. pH was controlled in the range of 3.5 to 3.8 by adjusting chlorine feed rate, and reaction temperature was controlled between 22° and 27°C. by circulating ice water through the reactor jacket. The product slurry, which overflows the side arm, is filtered to separate the crystalline product from the mother liquor, and is then dried in an oven at 100°C. The product slurry was observed to settle slowly and was filtered to 10 to 12% free moisture.

EXAMPLE 2

The example was conducted in a manner identical to that of Example 1 except for the presence of a promoter within the scope of the present invention. The promoter employed was "Pluronic L-62" polyoxyethylene-polyoxypropylene copolymer. The copolymer specific gravity is 1.03; the refractive index is 1.4550 at 25°C.; and the pour point is −4°C. A feed solution identical to that of Example 1 was prepared. A chlorination was conducted as described in Example 1 except that 200 ppm (based upon the reactor contents) of Pluronic L-62 polyoxyethylene-polyoxypropylene copolymer was introduced to the reaction. Part of this 200 ppm promoter addition was admitted to the initial reactor water charge and part was admitted to the feed solution. The resulting product slurry in this case was observed to settle rapidly and was filtered to 4–5% free moisture.

EXAMPLE 3

This example again illustrates the preparation of trichlorocyanuric acid with a promoter of the present invention. A feed solution identical to that of Example 1 was again prepared. A chlorination was carried out as described in Example 2 except that "Pluronic L-122" polyoxyethylene-polyoxypropylene copolymer was utilized as the promoter in the same concentration. This copolymer is said by the supplier to have an average molecular weight of 5,000 and to be approximately 20% ethoxylated. The product slurry was again observed to settle rapidly and was filtered to 4–5% free water.

The results of the above examples illustrate the superior dewatering properties attributable to the presence of a promoter of this invention. Without benefit of the promoter the trichlorocyanuric acid slurry exhibited more than 10% free moisture. With the promoter present during the reaction, however, the product slurry contained substantially less free moisture, e.g., 4–5%. Such reduced free water levels materially improve filtering and drying properties of the trichlorocyanuric acid product.

Consistent with the improved dewatering characteristics it was found that the particle size distribution of the dried product was substantially larger in those cases where the promoter was utilized. Particle size comparisons are set forth in TABLE I below wherein the results of Examples 1, 2 and 3 are compared.

TABLE I

| Screen Size Meshes per centimeter | Cumulative weight percent retained | | |
|---|---|---|---|
| | Example 1 | Example 2 200 ppm L-62 | Example 3 200 ppm L-122 |
| 15.7 | 0 | 4.2 | 35.6 |
| 23.6 | 0 | 91.2 | 85.4 |
| 39.4 | 30 | 95.4 | 97.0 |
| 78.7 | 65 | 96.5 | 98.3 |
| 128.0 | 83 | 98.3 | 99.3 |

EXAMPLE 4

The following example illustrates the preparation of dichlorocyanuric acid (dichloroisocyanuric acid) without benefit of the promoter of the present invention. The chlorination was carried out using the same equipment and the same procedure as in Example 1 above. The feed solution was prepared by mixing a cyanuric acid slurry with sodium hydroxide to produce a solution containing 9.8% cyanuric acid and having a sodium hydroxide to cyanuric acid mole ratio of 2.1:1. Feed solution was introduced to the reactor at about 60 ml./min. in the same manner as in Example 1. Chlorine was introduced at about 7.1 grams per minute to maintain a pH in the range of 2.1 to 2.3. The product was filtered and dried as in Example 1. The product slurry was filtered to 26% free water.

EXAMPLE 5

The following example describes the preparation of dichlorocyanuric acid according to the method of Example 4 except that a promoter of the present invention was employed. Dichlorocyanuric acid was prepared according to the method of Example 4 except that 200 ppm (based upon the reactor contents) of Pluronic L-62 polyoxyethylene-polyoxypropylene copolymer was added in part to the initial reaction charge and in part to the feed solution. The product slurry was filtered to 17% free water.

EXAMPLE 6

Dichlorocyanuric acid was prepared according to the process of Example 5 except that Pluronic L-122 promoter was substituted for Pluronic L-62 promoter in the same concentration. The product slurry was filtered to 19% free water.

A comparison of the particle size distribution of the respective dried products resulting from Examples 4, 5 and 6 is set forth in TABLE II below wherein the superior results achieved with promoters of the present invention are apparent.

TABLE II

| Screen Size Meshes per centimeter | Cumulative weight percent retained | | |
|---|---|---|---|
| | Example 4 | Example 5 200 ppm L-62 | Example 6 200 ppm L-122 |
| 39.4 | 0.9 | 49.8 | 47.1 |
| 78.7 | 16.3 | 83.5 | 78.7 |
| 106.2 | 25.0 | 86.6 | 82.9 |
| 128.0 | 38.7 | 89.3 | 88.1 |

In addition to copolymers of polyoxyethylene and polyoxypropylene, promoters of the present invention may include homopolymers of propylene oxide or of ethylene oxide. The following Example 7 illustrates the preparation of trichlorocyanuric acid wherein the reaction is carried out in the presence of a homopolymer of propylene oxide.

EXAMPLE 7

Equipment employed, feed solution preparation and chlorination are as described in Example 1 except that 200 ppm (based upon the reactor contents) of a homopolymer of propylene oxide was employed as the promoter and was added to the initial water charge and the feed solution. This homopolymer was supplied by Witco Chemical Company under the trade name "EMCOL CD-17". Results are presented in TABLE III.

Promoters of the present invention can be employed in admixture with other agents. The other agents may or may not contain ethylene oxide or propylene oxide within their molecular structure. An example of a co-promoter useful herein which contains ethylene oxide within the molecule is the product "STEROX NJ" manufactured by Monsanto Company. STEROX NJ is a nonylphenol-ethylene oxide condensate, more specifically, an alkylaryl polyoxyethylene ether. The following Example 8 illustrates the preparation of trichlorocyanuric acid in the presence of a promoter which comprises a mixture of STEROX NJ and a homopolymer of propylene oxide.

EXAMPLE 8

The process was conducted as described in Example 7 except that 150 ppm of EMCOL CD-17 and 50 ppm of STEROX NJ were substituted for the 200 ppm of EMCOL CD-17 of Example 7.

A comparison of the particle size distribution of the respective dried products resulting from Examples 1, 7 and 8 is presented in TABLE III. Superior results achieved from the use of promoters of the present invention are apparent.

TABLE III

| Screen Size Meshes per centimeter | Cumulative weight percent retained | | |
|---|---|---|---|
| | Example 1 | Example 7 200 ppm CD-17 | Example 8 150 ppm EMCOL CD-17/50 ppm STEROX NJ |
| 23.6 | 0 | 35.7 | 68.0 |
| 39.4 | 30 | 74.4 | 84.7 |
| 78.7 | 65 | 89.9 | 94.4 |
| 128.0 | 83 | 95.1 | 97.1 |

From a consideration of the results set forth above, it is apparent that considerable latitude is afforded in selection of the promoter as well as its concentration in the aqueous reaction medium or in the chlorinator. For example, polyoxyethylene-polyoxypropylene copolymers useful herein may vary widely in average molecular weight. A preferred average molecular weight range is 1,000 to 6,000. Copolymers ranging below 1,000 may tend to exhibit inadequate hydrophilic properties while those over 6,000 may be susceptible to gelation.

A preferred range of ethoxylation within the polyoxyethylene-polyoxypropylene copolymers of this invention is about 10 to about 30% by weight although higher ethoxylation can be tolerated in many cases. Thus, while the illustrated polyoxyethylene-polyoxypropylene copolymers were approximately 20% ethoxylated, this figure can vary significantly while still achieving improved results.

While less than 20 ppm concentration of the promoter based upon the reactor contents is functional, more significant results are achieved when the concentration is between 20 and 500 ppm. Although promoter concentrations above 500 ppm would produce satisfactory results, not enough improvement could be expected to offset the economic disadvantages.

Many complex promoters other than STEROX NJ which contain polyoxyethylene or polyoxypropylene in the molecule are also considered useful for purposes of the present invention. Like STEROX NJ, such complex compounds may be advantageously used alone or in admixture with the preferred promoters herein. For example, ethylene oxide-type condensates containing alkylaryl groups other than nonylphenol may be employed.

In adapting the process of this invention to certain continuous manufacturing operations, it may be desirable to introduce the promoter directly to the chlorinator and not to the feed solution in order to increase the efficiency of the promoter.

It was surprising that the superior promoters of the present invention did not decompose during the reaction before achieving their desired effect. It was also surprising that the promoter's presence could not be traced in some degree to the final chlorocyanuric acid product. Both of these features are desirable but were completely unexpected in a reaction of this type.

While this invention has been described with respect to specific examples and embodiments, it is to be understood that the invention is not limited thereto and that it can be variously practiced within the scope of the following claims.

The embodiments of this invention in which an exclusive property or privilege is claimed are defined as follows:

1. In a process for preparing a chlorocyanuric acid selected from the group consisting of dichlorocyanuric acid, trichlorocyanuric acid and mixtures thereof by the reaction of cyanuric acid with alkali metal hydroxide and chlorine in an aqueous reaction mixture and recovering the acid product from said reaction mixture, the improvement which comprises conducting the reaction in the presence of a promoter selected from the group consisting of polyoxyethylene, polyoxypropylene, and polyoxyethylene-polyoxypropylene copolymers.

2. A process of claim 1 wherein the promoter concentration is from 20 to about 500 ppm by weight based upon the reactor contents.

3. A process of claim 1 wherein the alkali metal hydroxide is sodium hydroxide.

4. In a process for preparing trichlorocyanuric acid by the reaction of cyanuric acid with sodium hydroxide and chlorine in an aqueous reaction mixture and recovering the acid product from said reaction mixture, the improvement which comprises conducting the reaction in the presence of from about 100 to about 300 ppm by weight of a polyoxyethylene-polyoxypropylene copolymer, based upon the reactor contents.

5. A process of claim 4 wherein the average molecular weight of said copolymer is from about 1,000 to about 6,000.

6. A process of claim 4 wherein the ethoxylation level of said copolymer is from about 10 to about 30% by weight.

7. In a process for preparing a chlorocyanuric acid selected from the group consisting of dichlorocyanuric acid, trichlorocyanuric acid and mixtures thereof by the reaction of cyanuric acid with alkali metal hydroxide and chlorine in an aqueous reaction mixture, the improvement which comprises conducting the reaction in the presence of a nonylphenol-ethylene oxide condensate.

8. A process of claim 7 wherein said condensate is present in about 20 to about 500 ppm by weight based upon the reactor contents.

* * * * *